(12) United States Patent
Quiroga et al.

(10) Patent No.: US 8,851,431 B2
(45) Date of Patent: Oct. 7, 2014

(54) ANATOMIC SUPPORT FOR HAND

(75) Inventors: Lecy Maria Vasconcelos Quiroga, Rio de Janeiro (BR); Ricardo da Cunha Fontes, Rio de Janeiro (BR); Marco Aurelio Lopes Ramalho, Rio de Janeiro (BR); Mario Luiz Novaes Avila, Rio de Janeiro (BR)

(73) Assignee: Marrio Luiz Novaes Avila, Rio de Janeiro (BR)

( * ) Notice: Subject to any disclaimer, the term of this patent is extended or adjusted under 35 U.S.C. 154(b) by 586 days.

(21) Appl. No.: 12/982,188

(22) Filed: Dec. 30, 2010

(65) Prior Publication Data
US 2011/0095142 A1    Apr. 28, 2011

Related U.S. Application Data

(63) Continuation-in-part of application No. 11/663,148, filed as application No. PCT/BR2004/000254 on Dec. 29, 2004, now Pat. No. 7,861,984.

(30) Foreign Application Priority Data

Sep. 16, 2004  (BR) ...................................... 0403892
Sep. 16, 2004  (BR) ...................................... 0404007

(51) Int. Cl.
*B68G 5/00*    (2006.01)
*A61F 5/30*    (2006.01)

(52) U.S. Cl.
CPC ................ *A61F 5/30* (2013.01); *Y10S 248/918* (2013.01)
USPC ..................... 248/118; 248/118.1; 248/118.5; 248/918; 400/715

(58) Field of Classification Search
USPC ............ 248/118, 118.1, 118.5, 918; 400/715
See application file for complete search history.

(56) References Cited

U.S. PATENT DOCUMENTS

| 105,001 | A | * | 7/1870 | Sanborn ...................... 248/118.5 |
| 3,300,250 | A | | 1/1967 | Dollgener et al. |
| 4,576,351 | A | * | 3/1986 | Brink ............................ 248/118 |
| 4,862,165 | A | | 8/1989 | Gart |
| 5,163,646 | A | | 11/1992 | Engelhardt |
| 5,228,655 | A | | 7/1993 | Garcia et al. |
| 5,234,186 | A | * | 8/1993 | Powell ........................ 248/118.1 |
| 5,242,139 | A | | 9/1993 | Aldrich |

(Continued)

FOREIGN PATENT DOCUMENTS

| DE | 29919297 U1 | 3/2000 |
| DE | 29919434 U1 | 4/2000 |

(Continued)

OTHER PUBLICATIONS

PCT International Search Report for PCT/BR2004/000254 dated May 11, 2005.

*Primary Examiner* — Terrell McKinnon
*Assistant Examiner* — Michael McDuffie
(74) *Attorney, Agent, or Firm* — Nevrivy Paent Law Group P.L.L.C.

(57) ABSTRACT

An anatomic support for hand and wrist includes a body having an upper surface, a side surface and an inferior surface. The upper surface has a shape that enables a user that operates a keyboard or the like to place his/her hand on said upper surface so as to have his/her wrist and hand permanently and anatomically supported.

24 Claims, 5 Drawing Sheets

(56) References Cited

U.S. PATENT DOCUMENTS

| | | | |
|---|---|---|---|
| 5,265,835 A * | 11/1993 | Nash | 248/118 |
| 5,349,192 A | 9/1994 | Mackay | |
| 5,370,346 A * | 12/1994 | Long | 248/118.5 |
| 5,398,896 A * | 3/1995 | Terbrack | 248/118.5 |
| 5,472,161 A | 12/1995 | Krukovsky | |
| 5,566,913 A | 10/1996 | Prokop | |
| 5,568,907 A * | 10/1996 | Wolfe et al. | 248/118 |
| 5,678,266 A | 10/1997 | Petringa et al. | |
| 5,730,711 A | 3/1998 | Kendall et al. | |
| 5,762,302 A * | 6/1998 | Myers | 248/118.5 |
| 5,803,416 A | 9/1998 | Hanson et al. | |
| 5,865,404 A | 2/1999 | Hesley | |
| 5,892,499 A | 4/1999 | Vulk, Jr. | |
| 5,913,497 A * | 6/1999 | Myers | 248/118.5 |
| 5,918,839 A * | 7/1999 | DuBois | 248/118 |
| 5,954,303 A | 9/1999 | Wolf et al. | |
| 5,980,143 A | 11/1999 | Bayer et al. | |
| 6,017,006 A | 1/2000 | Cherubini et al. | |
| 6,032,913 A | 3/2000 | Dawson | |
| 6,048,325 A | 4/2000 | Kendall et al. | |
| 6,082,682 A | 7/2000 | So et al. | |
| 6,082,684 A | 7/2000 | Chuang | |
| 6,089,516 A | 7/2000 | Yates | |
| 6,219,867 B1 | 4/2001 | Yates | |
| 6,293,026 B1 | 9/2001 | Lee et al. | |
| 6,328,266 B1 | 12/2001 | Yates | |
| 6,362,811 B1 | 3/2002 | Edwards et al. | |
| 6,492,975 B1 | 12/2002 | Weiss | |
| 6,494,418 B1 | 12/2002 | Wolf et al. | |
| 6,499,703 B2 | 12/2002 | Chou | |
| 6,506,271 B1 | 1/2003 | Yates | |
| 6,663,056 B1 | 12/2003 | Lee | |
| 6,672,548 B1 | 1/2004 | Yates | |
| 6,726,158 B2 | 4/2004 | Issa | |
| 2002/0130226 A1 * | 9/2002 | Nogueira | 248/118.5 |
| 2002/0162919 A1 | 11/2002 | Kuo | |
| 2003/0169236 A1 | 9/2003 | Crocker | |
| 2003/0209641 A1 | 11/2003 | Cooke | |

FOREIGN PATENT DOCUMENTS

| | | |
|---|---|---|
| FR | 2812108 | 1/2002 |
| WO | 99/05062 | 2/1999 |
| WO | 00/57749 | 10/2000 |

\* cited by examiner

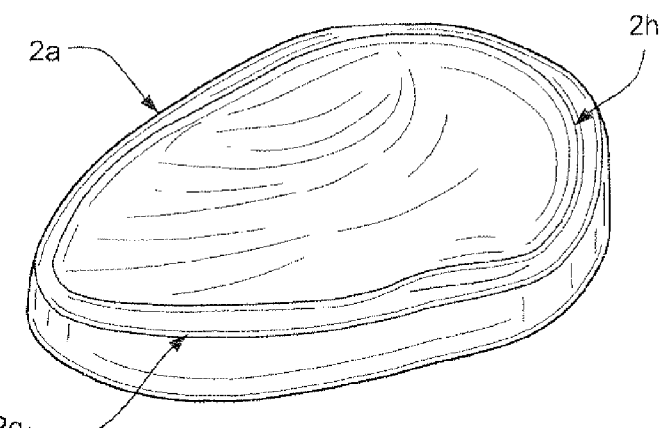
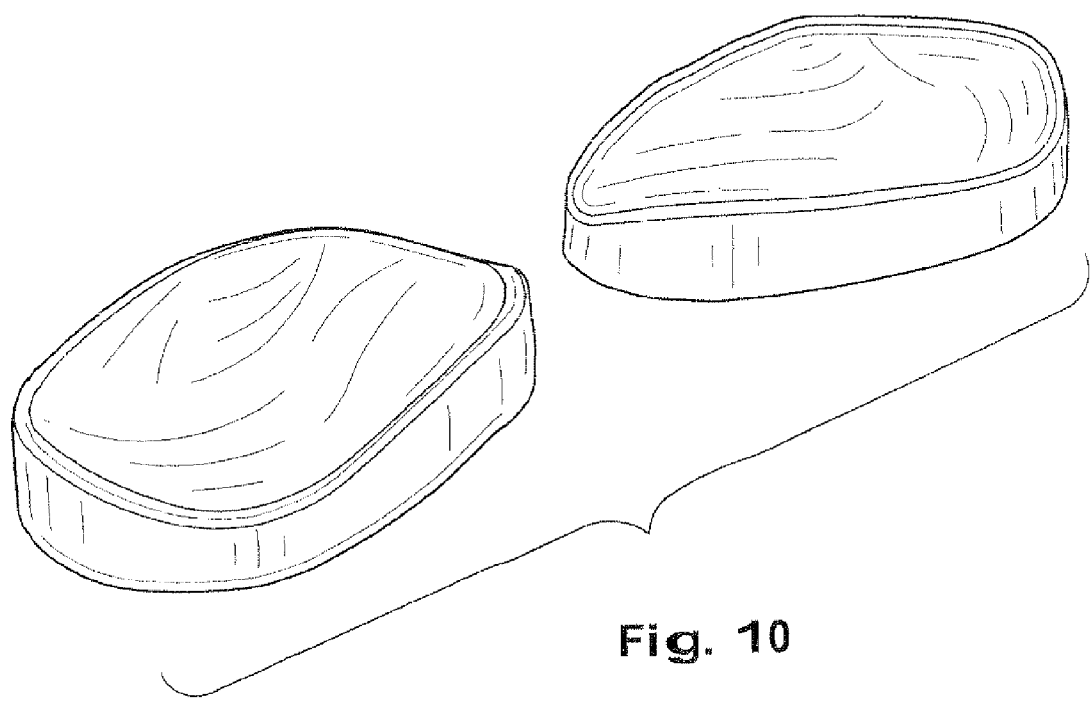

ANATOMIC SUPPORT FOR HAND

This application is a continuation-in-part of U.S. application Ser. No. 11/663,148, filed Mar. 16, 2007 U.S. Pat. No. 7,861,984, which in turn is the US National Stage Application of International Application No. PCT/BR2004/000254 filed Dec. 29, 2004 which designated the U.S. and claims priority to Brazilian Application No. 0404007-4, filed Sep. 16, 2004 and Brazilian Application No. 0403892-4, filed Sep. 16, 2004, the entire contents of each of which are hereby incorporated herein by reference.

FIELD OF THE INVENTION

The present invention relates to a support for both the hand and the wrist of an individual who uses a keyboard of a computer. More specifically, the present invention relates to a support for hand and wrist which is provided with anatomical features in order to provide substantial support for the hands and the wrist of a user who uses a keyboard or the like.

RELATED ART

Individuals who execute tasks involving excessive, continuous and repetitive efforts, without periodically stopping for rest, may eventually develop a disease known as Repetitive Strain Injury—RSI.

The acronym RSI relates to a group of diseases which mainly affect the upper extremities, shoulders, wrist and hands, causing irritation, swelling and damage to tendons, nerves, muscles, and other soft body tissues. Injuries such as RSI are usually caused by repeated and continuous physical movements, which cause an excessive load to the muscles, beyond their inherent capacity for immediate recovery. Bad sitting posture, stress, and bad working conditions also contribute for the development of RSI.

In extreme cases, RSI can cause serious injuries to the tendons, extreme pain and loss of movements. RSI encompasses a number of diseases, such as tenosynovitis, tendinitis, epicondylitis, carpal tunnel syndrome, bursitis, etc. RSI is also known by many experts as osteo-muscular work-related disorders. Another designation for RSI is Cumulative Trauma Disorder.

Injuries such as RSI cause serious problems both to employees and employers, as increasingly a number of workers become inactive for long terms due to RSI injuries.

In recent years the growing use of personal computers in almost all the professional and educational activities has caused a significantly growing number of persons suffering from RSI, fundamentally as a consequence of the need to use keyboards to enter data and to operate the computers. Such operation is known as typing.

It is widely known that the typing operation, in view of its inherent repeated and continuous physical movements, can cause serious injuries to those individuals who must operate keyboards for large portions of their lives as part of their professional activities.

Typing operations are characterized by the execution of small, continuous and fast movements with the fingers. Over the long term, such typing operations can cause an overload in the muscles, muscular fasciae, blood vessels, tendons, ligaments, articulations and nerves of the hands of a person who types in such conditions. Frequently such overloads cause serious RSI injuries in persons who work in the above-mentioned conditions.

It is noted that a lack of a support for the hands and wrist of a typist is the main cause contributing to RSI injuries.

Although RSI-like injuries in typists have been well known for years, there have been few efforts to search for solutions which do away with or mitigate the nasty effects of RSI-like injuries in typists.

It is known in the art to use a wedge-like piece attached to the forward part of the keyboard, where the wrist of the typist rest, said wedge-like piece serving as a support for the wrists.

The use of such wedge-like piece has proved to be inefficient to solve the problem, as besides being incommodious it serves only as a support for the wrist of the typist, leaving the palm of the hands of the typist unsupported. As this wedge-like piece is inefficient and incommodious, the typists usually detach it from the keyboard and simply type on the keyboard without using it.

U.S. Pat. No. 5,439,192, published on 8 Aug. 1995 and entitled "Hand-worn device for elevating the hand and fingers with respect to a keyboard", discloses a device for encircling the base portion of a user's hand and for elevating that hand and the associated fingers with respect to a keyboard. Said device is provided with a pliable and elastic cuff that encircles the base of the hand and which includes a thumb opening, through which the thumb of the hand projects.

The cuff specifically encircles and wraps around the lower base of the hand and particularly wraps around and covers the heel of the hand. An attachable and relatively small elevating pad is provided, designed to attach directly to the cuff in the area adjacent the heel of the hand. The elevating pad is substantially as high as the keyboard, so as to keep the hands of the typist at the same level of the keys of the keyboard.

Although the device disclosed in U.S. Pat. No. 5,439,192 is able to provide a support for the wrist of the typist, it is inefficient to provide a substantial support for the palms of the hands and therefore it is inefficient to prevent RSI-like injuries from occurring.

It should be also mentioned that the device disclosed in U.S. Pat. No. 5,439,192 is incommodious, as it is necessary to permanently use the cuff around the lower base of the hand, and this can inconvenience the typist when he/she has to use the hands to do another task, such as writing with a pen, answering a phone call, etc., which would require the typist to remove the elevating pad from the cuff.

It should be also mentioned that the cuff itself is uncomfortable to perform the typing task, and in case the cuff is too tight it can cause problems with blood circulation in the wrist and the hands of the typist. Therefore, instead of being a kind of prevention for RSI, the device disclosed in U.S. Pat. No. 5,439,192 can otherwise aggravate the RSI injury.

U.S. Pat. No. 5,398,896, published on 21 Mar. 1995, discloses a device consisting an extremely complex structure comprising a number of components attached thereto and intended to allow an user of a keyboard to place his/her hands on a support member designed to accommodate the hands and wrist of such an user in a higher position with respect to the level of the keys of the keyboard.

The device of U.S. Pat. No. 5,398,896 comprises an elongate guide track having a pair of elongate support arms pivotally connected thereto which are selectively extensible into generally perpendicular relation to the track and are sized and configured to support a keyboard when extended. Each of the support arms includes an adjustment mechanism attached thereto for selectively adjusting the height of the keyboard relative the guide track.

The device of U.S. Pat. No. 5,398,896 further comprises a pair of support assemblies connected to the guide track and adapted to support a user's forearms, wrist and hands thereon. Each of the support assemblies comprises a carriage member which is slidably engaged to the guide track and movable longitudinally there along. The carriage member itself comprises a housing defining first, second and central portions and a pair of axle members extending laterally through the first portion of the housing in substantially parallel relation. Attached to the opposed ends of the axle members are first and second pairs of rollers or wheels.

Pivotally connected to the carriage member, and more particularly to the second portion of the housing, is a linkage member, while pivotally connected to the linkage member is a support member preferably formed of unitary construction and specifically sized and configured to support the user's forearm and wrist as well as the palm surface of the user's hand. The pivotal connection of the carriage member and the support member to the linkage member and the slidable engagement of the carriage member to the guide track facilitates dynamic lateral and longitudinal movement of the support member relative the track.

The device disclosed in U.S. Pat. No. 5,398,896, besides being extremely complex, requires the user to make a complicated and time consuming assembly before it can be used, as well as other drawbacks.

First, the fact that the hand of the user is kept in a level substantially higher than the level of the keys of the keyboard causes the user to turn down his hands to type on the keyboard which is totally inappropriate for the user. By repeating the typing operation for long periods of time the user can suffer from a RSI-like injury.

Second, at the time when U.S. Pat. No. 5,398,896 was filed (1993), the use of mice in personal computers was uncommon. The use of a mouse nowadays is extremely frequent, consuming in some cases long periods of time. In such situations the user must raise his/her hands from the support to use the mouse, keeping his/her hand unsupported in the whole interim. When such an operation is frequently repeated it can cause a RSI-like injury to occur.

Therefore, the device disclosed in U.S. Pat. No. 5,398,896 fails to provide a permanent and anatomic support for the hands and wrist of a user who operates a keyboard.

U.S. Pat. No. 6,048,325, published on 11 Apr. 2000, discloses a device including a huge number of components attached thereto, basically consisting of a body which comprises a lower portion attached to a generally convex resilient upper portion.

A cavity is formed between the lower portion and the generally convex upper portion, and a padding element is inserted into said cavity. When a user rests his/her hand on the generally convex resilient upper portion, it causes said resilient upper portion to deform so as to accommodate the hand of the user therefore making a pressure on the padding element.

The device of U.S. Pat. No. 6,048,325 is able to slide upon the surface where it rests when the user moves his hand to type a keyboard.

Although the device of U.S. Pat. No. 6,048,325 is intended to provide a typing support for the palm of the hand of a user who types on a keyboard, it has some drawbacks which causes it to be inefficient to substantially provide a permanent and concomitant anatomic support for both the palm of the hand and wrist of a user.

A first drawback is the fact that the padding element provides a permanent upward force when a user rests his/her hands on the generally convex resilient upper portion. When the weight of the hand of the user is not higher than said upward force so as to substantially cause the generally convex resilient upper portion to substantially deform, in order to concomitantly accommodate both the palm of the hand and the wrist of the user, there is a possibility that the hand of the user slides on the generally convex resilient upper portion, especially when the hand of the user is sweaty or greasy. This could hamper the typing operation or even cause the user to stop it.

Moreover, in such situation there is a strong possibility that the user has to press downwards on the generally convex resilient upper portion in order to ensure that his/her hand remains in a fixed position on the support. This is totally inadequate as the user besides to type the keyboard has also to make an additional physical effort to press the resilient upper portion.

When the user has frequently to repeat the typing operation in such improper circumstances, it can cause a RSI-like injury to occur.

Another drawback of the device of U.S. Pat. No. 6,048,325 is that there is nothing in the device to guide the user to place his/her hand on to the generally convex resilient upper portion in such a way that the palm of the hand and the wrist are concomitantly supported on said resilient upper portion.

This can cause the hand and the wrist of the user to become misplaced, therefore being not concomitantly and anatomically supported onto the generally convex resilient upper portion. For that reason, there is a strong tendency for the user to place only the palm of his/her hand onto the generally convex resilient upper portion, and so the wrist becomes unsupported during the typing operation.

Again, when the user has frequently to repeat the typing operation in such improper circumstances it can cause a RSI-like injury to occur.

Therefore, the device of U.S. Pat. No. 6,048,325 is inappropriate to provide a safe, permanent and concomitant anatomic support for both the palm of the hand and the wrist of a user.

SUMMARY OF THE INVENTION

The present invention relates to an anatomic support for the hand and wrist which permanently and concomitantly accommodates the anterior part of the palm and the wrist of a user operating a keyboard or the like.

The anatomic support object of the present invention comprises an upper surface, a side surface and an inferior surface. The upper surface is provided with a shape which enables the wrist and the anterior portion of the palm of the hand of a user operating a keyboard to be permanently and concomitantly supported, while resting anatomically onto the upper surface.

A central portion of the upper surface of the anatomic support for hand and wrist is provided with a generally convex front protruding region, which serves as an anatomical abutment for the generally concave central region of the palm of the hand of a user operating a keyboard.

The upper surface is also provided with a central depression encircling the front protruding region and serving to permanently and anatomically accommodate the protruding back portion of the anterior part of the palm of the hand of a user.

Furthermore the back border portion of the upper surface is provided with a back border upward segment serving to permanently and anatomically accommodate the wrist of the user. A side upward segment is also provided onto the upper region and serves to permanently and anatomically accommodate the external side portion of the anterior region of the hand of a user.

Therefore the front protruding region, the central depression, the back border upward segment and the side upward segment cooperate to provide the upper surface with a shape that permanently and anatomically accommodates the anterior region of the palm of the hand and the wrist of a user.

The height of the side surface of the anatomic support is such that the tips of the fingers of a user remain at a level substantially equal to the level of the keys of a keyboard. This prevents the user from bending his/her hands upward or downward when is typing the keyboard.

The body of the anatomic support can be solid or partially or fully hollow. When the body of the anatomic support is hollow, internal reinforcement ribs can be provided to strengthen the anatomic support for hand and wrist.

Furthermore, the anatomic support can be provided with bottom protrusions which serve to prevent the entire inferior surface from contacting the surface upon which the anatomic support for hand and wrist rests, thereby reducing friction forces.

BRIEF DESCRIPTION OF THE DRAWINGS

The invention will be described in detail hereupon, together with the attached drawings which are part of the present specification, for the purpose of exemplification only.

FIG. 9 is a top perspective view of the support for hand and wrist object of the present invention.

FIG. 10 is a top perspective view of a pair of supports for hand and wrist objects of the present invention.

DETAILED DESCRIPTION OF THE INVENTION

The invention refers to an anatomic support for hand and wrist 1 intended to support the hands and the wrist of a user operating a computer keyboard or the like.

Figure 1:
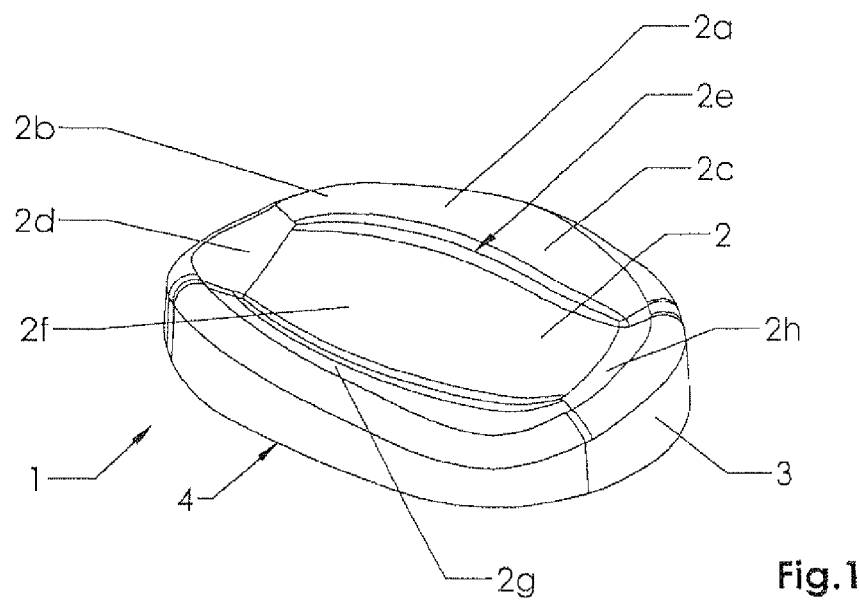
FIG. 1 is a top perspective view of the support for hand and wrist object of the present invention.
Figure 2:
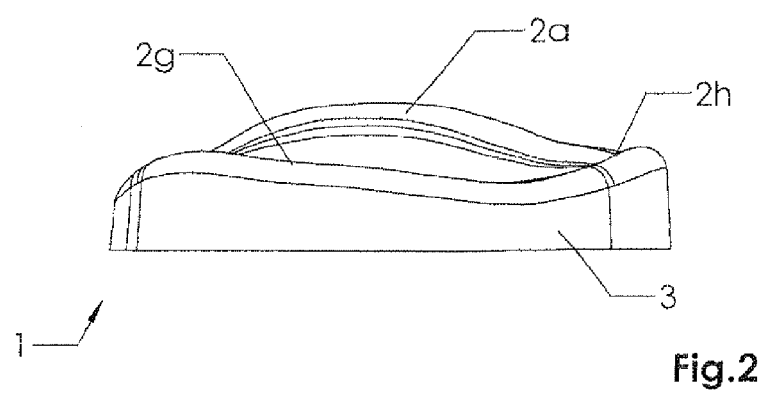
FIG. 2 is a side view of the support for hand and wrist of FIG. 1.

FIGS. 1 and 2 depict an anatomic support for hand and wrist 1 comprising a body having an upper surface 2, a side surface 3 and an inferior surface 4.

The upper surface 2 of the anatomic support for hand and wrist 1 is provided with a shape that enables a user operating a keyboard or the like to place his/her hand on said upper surface 2 so as to have his/her wrist and hand permanently and anatomically supported.

With that aim, the upper surface 2 is provided with a front border protruding region 2a, located at its front border portion and serving to permanently provide an anatomic support for the anterior part of the palm of the hand of the user that places his/her hand on the upper surface 2 of the anatomic support for hand and wrist 1.

The front border protruding region 2a is provided at its central border section with a central segment 2b; a right descending segment 2c, which descends from the central segment 2b to the right side of the front border protruding region 2a; a left descending segment 2d, which descends from the central segment 2b to the left side of the front border protruding region 2a; and a central descending segment 2e, which descends from the central segment 2b to the center of the upper surface 2.

Said central segment 2b, right descending segment 2c, left descending segment 2d and central descending segment 2e provides the front border protruding region 2a with a generally convex shape which anatomically conforms with the generally concave shape of the center to back portion of the palm of the hand of a user that places his/her hand on the upper surface 2 of the anatomic support for hand and wrist 1.

The upper surface 2 in its center to back portion is also provided with a depression 2f of a generally concave shape encircling the front border protruding region 2a and serving to permanently and anatomically accommodate the protruding back portion of the hand of the user.

The back border portion of the upper surface 2 is provided with a back border upward segment 2g serving to permanently and anatomically accommodate the wrist of the user. Furthermore, a side upward segment 2h is provided with at the center to side border portion of the upper surface 2 and serving to permanently and anatomically accommodate the external side portion of the anterior region of the palm of the user.

Therefore the front protruding region 2a, the central depression 2f, the back border upward segment 2g and the side upward segment 2h cooperate to provide the upper surface 2 with a shape that permanently and anatomically accommodates the anterior region of the palm of the hand and the wrist of an user who operates a keyboard, thereby helping to prevent RSI-like injuries from occurring.

FIG. 9 depicts an upper perspective view of the support for hand and wrist 1 object of the present invention. FIG. 9 shows the detailed contours of the front protruding region 2a, the central depression 2f, the back border upward segment 2g and the side upward segment 2h.

As the upper surface 2 anatomically accommodates the anterior portion of the palm of the hand and of the wrist of a user, and as the left and right hands are provided with substantially similar shapes but rotated at 180°, as a mirror image, this causes the need to provide anatomic supports for hand and wrist 1 having upper surfaces 2 tailored for the left and right hands. The user must use a pair of anatomic supports for hand and wrist 1 when typing on a keyboard or the like, one for the left hand and another for the right hand.

As a consequence of the upper surfaces 2 being tailored to the left and right hands, if user places one of his/her hands and wrist on an anatomic support for hand and wrist 1 intended for the use of the other hand, the user will never manage to anatomically accommodate his hand and wrist on the upper surface 2 of the anatomic support for hand and wrist 1. The user will immediately recognize having placed his hand on a anatomic support for hand and wrist 1 intended for the use of the other hand.

To avoid such situations from occurring an anatomic support for hand and wrist 1 can be provided with some indicative symbol or the like in order to inform the user about which hand it is intended to support.

FIG. 10 depicts an upper perspective view of a pair of left and right supports for hand and wrist 1 object of the present invention.

Figure 11:
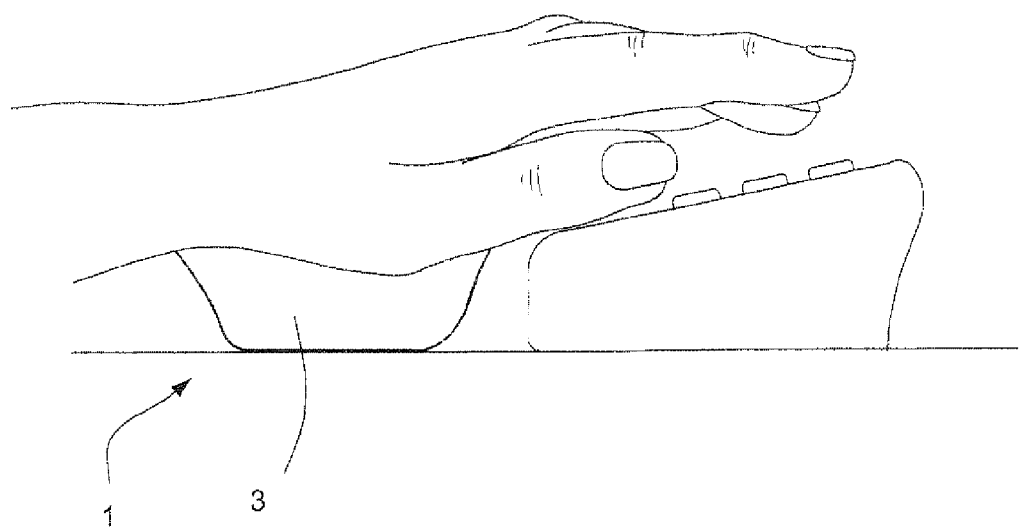
FIG. 11 is a side view of the support for hand and wrist object of the present invention, taken from the right, showing the hand of a user resting on the support and operating a keyboard.

FIG. 11 is a side view of the support for hand and wrist object of the present invention, taken from the right, showing the hand of a user resting on the support and operating a keyboard.

There are a number of causes for RSI-like injuries to occur and one of them is the fact that a user of a keyboard frequently has to bend upwardly or downwardly his/her wrist when typing on a keyboard. When a typing operation is repeatedly made in such conditions, there is a strong possibility that a RSI-like injury eventually occurs.

The height of the side surface 3 of the anatomic support for hand and wrist 1 is such that it enables the tips of the fingers of the user to remain at a level substantially equal to the level of the keys of the keyboard. This prevents the user from bending his/her hands upwardly or downwardly when typing on the keyboard.

A further advantage for the use of the anatomic support for hand and wrist 1 is that besides providing the user with a permanent and anatomic support for his/her hands and wrist, it also enables the user to use a mouse while simultaneously keeping his/her hand and wrist on the anatomic support for hand and wrist 1.

In other words, the user need not remove his/her hand from the support for hand and wrist 1 when he/she needs to use a mouse. It is possible to operate the mouse and simultaneously keep his/her hand permanently and anatomically accommodated on the upper surface 2 of the anatomic support for hand and wrist 1.

When the user has to interrupt a typing operation to use a mouse, then he/she has simply to displace his/her hand towards the mouse and operate it, keeping his hand and wrist permanently and anatomically accommodated on the anatomic support for hand and wrist 1.

Therefore, irrespective of being typing or using the mouse, the user of the anatomic support for hand and wrist 1 will always have his/her hands and wrist permanently and anatomically accommodated on the upper surface 2 of the anatomic support for hand and wrist 1. This helps to prevent RSI-like injuries from occurring.

The inferior surface 4 shall be designed to cause low friction forces between the anatomic support for hand and wrist 1 and the surface upon which it rests when the anatomic support for hand and wrist 1 is displaced by the hand of the user who is typing on a keyboard or is operating a mouse.

When the whole inferior surface 4 contacts the surface where the anatomic support for hand and wrist 1 rests, then the inferior surface 4 must be smooth so as to cause low friction forces.

The inner portion of the body of the anatomic support for hand and wrist 1 can be solid or hollow at its bottom part, thereby forming a hollow portion. When the anatomic support for hand and wrist 1 is hollow, the surface area of the inferior surface 4 is consequently reduced, becoming simply a rim portion. This substantially reduces the friction forces between the inferior surface 4 and the surface where the anatomic support for hand and wrist 1 slides when the user is typing or using the mouse.

Furthermore, the anatomic support for hand and wrist 1 can be provided with bottom protrusions which serve to contact the surface upon which the anatomic support rests, preventing all of the inferior surface 4 from contacting said surface, and thereby reducing the friction forces.

Consequently both the small movements usually made by the hand of a user when typing on a keyboard and the movements needed to operate a mouse are facilitated by the fact that the friction forces are reduced, as no additional physical effort is needed to perform such movements.

Figure 3:
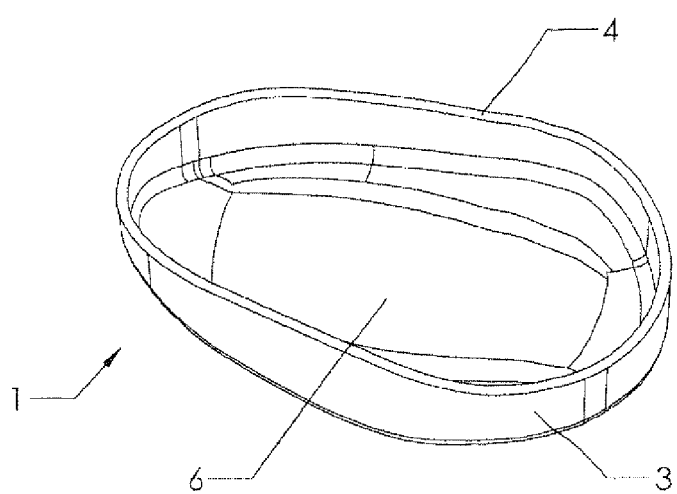
FIG. 3 is a bottom perspective view showing a first embodiment of the support for hand and wrist object of the present invention.

FIG. 3 is a bottom perspective view showing a first embodiment of the support for hand and wrist 1 object of the present invention. In this first embodiment, the inner portion of the body of the anatomic support for hand and wrist 1 is hollow, forming a hollow portion, in order to reduce the weight of the anatomic support for hand and wrist 1. The inferior surface 4 comprises only a rim portion.

Figure 4:
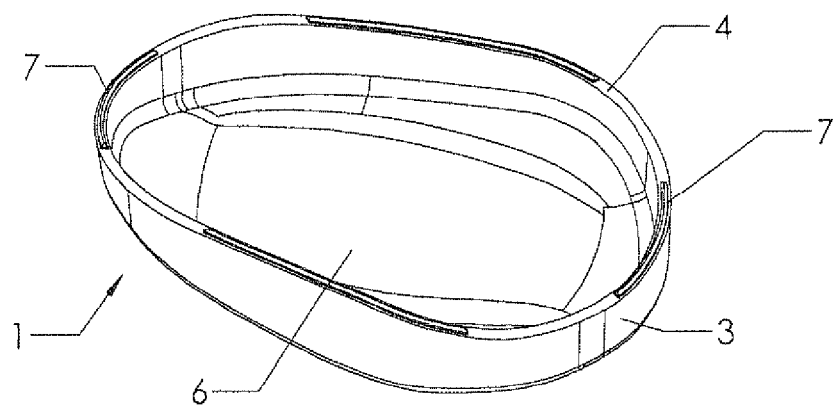
FIG. 4 is a bottom perspective view showing a second embodiment of the support for hand and wrist object of the present invention.

FIG. 4 is a bottom perspective view showing a second embodiment of the support for hand and wrist 1 object of the present invention. This second embodiment is similar to the embodiment of the anatomic support for hand and wrist 1 depicted in FIG. 3, but in this embodiment the inferior surface 4 is provided with bottom protrusions 7 intended to reduce the contact area between the inferior surface 4 and the surface upon which the anatomic support for hand and wrist 1 rests, thereby reducing the friction forces.

The number of bottom protrusions 7 used in this embodiment and its shape will depend on design parameters.

Figure 5:
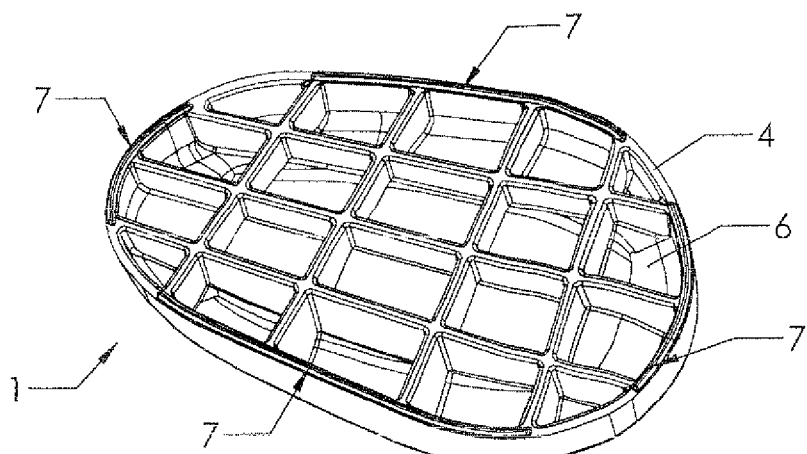
FIG. 5 is a bottom perspective view showing a third embodiment of the support for hand and wrist object of the present invention.

FIG. 5 is a bottom perspective view showing a third embodiment of the support for hand and wrist 1 object of the present invention. In this embodiment, the inner portion of the body of the anatomic support for hand and wrist 1 is hollow, like the previous embodiments, forming a hollow portion. The inferior surface 4 comprises only a rim portion. Reinforcement ribs 5 are provided in said hollow portion to strengthen the body of the anatomic support for hand and wrist 1.

In this embodiment, the reinforcement ribs 5 extend transversally and longitudinally with respect to the hollow portion, and pits 6 are formed between the reinforcement ribs 5. Anyone skilled in the art would immediately recognize that other types of reinforcement ribs 5 can be used to strengthen the body of the anatomic support for hand and wrist 1.

Bottom protrusions 7 are provided in the inferior surface 4 to minimize the contact between the anatomic support for hand and wrist 1 and the surface where it rests, thereby reducing the friction forces. Again, the number of bottom protrusions 7 used in this embodiment and its shape will depend on design parameters.

Figure 6:
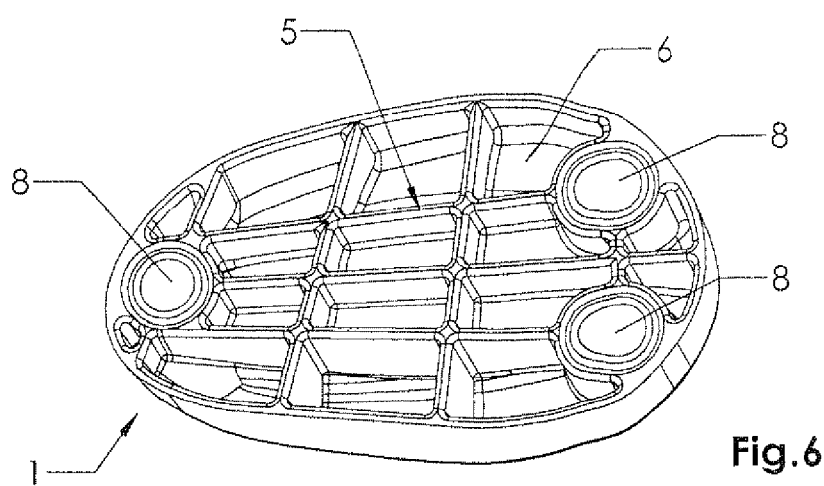
FIG. 6 is a bottom perspective view showing a fourth embodiment of the support for hand and wrist object of the present invention.

FIG. 6 is a bottom perspective view showing a fourth embodiment of the support for hand and wrist 1 object of the present invention. In this embodiment, the inner portion of the body of the anatomic support for hand and wrist 1 is hollow, like the previous embodiments, forming a hollow portion, and the inferior surface 4 comprises only a rim portion.

Reinforcement ribs 5 are provided in said hollow portion to strengthen the body of the anatomic support for hand and wrist 1, and pits 6 are formed between the reinforcement ribs 5.

Bottom protrusions 8 of a generally convex shape project from the reinforcement ribs 5, to minimize the contact between the inferior surface 4 and the surface where the anatomic support for hand and wrist 1 rests, thereby reducing the friction forces. Again, the number of bottom protrusions 8 used in this embodiment and its shape will depend on design parameters.

Figure 7:
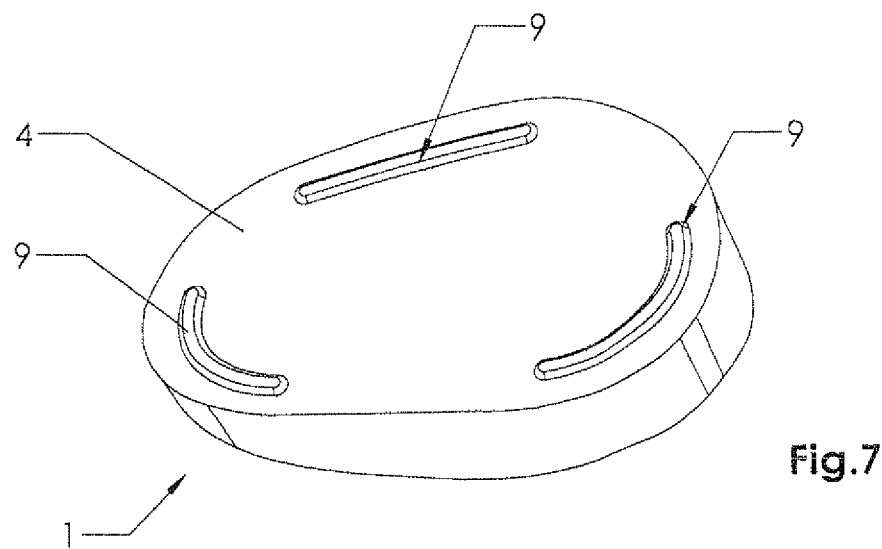
FIG. 7 is a bottom perspective view showing a sixth embodiment of the support for hand and wrist object of the present invention.

FIG. 7 is a bottom perspective view showing a fifth embodiment of the support for hand and wrist 1 object of the present invention. In this embodiment, the inner portion of the body of the anatomic support for hand and wrist 1 is solid and the inferior surface 4 is provided with elongate bottom protrusions 9. The number of bottom protrusions 9 used in this embodiment and its shape will depend on design parameters.

Figure 8:
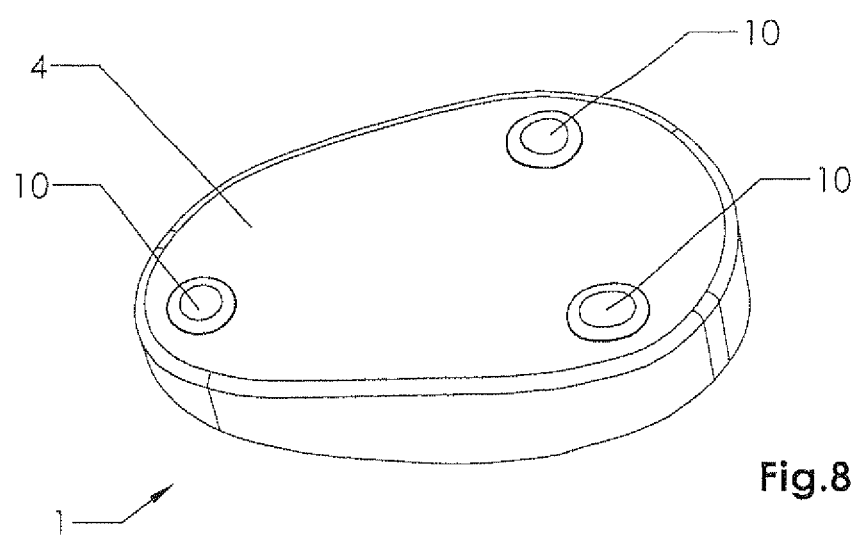
FIG. 8 is a bottom perspective view showing a seventh embodiment of the support for hand and wrist object of the present invention.

FIG. 8 is a bottom perspective view showing a sixth embodiment of the support for hand and wrist 1 object of the present invention. In this embodiment, the inner portion of the body of the anatomic support for hand and wrist 1 is solid and the inferior surface 4 is provided with bottom protrusions 10 of generally convex shape. The number of bottom protrusions 10 used in this embodiment and its shape will depend on design parameters.

The bottom protrusions 7, 8, 9, 10 provided in the embodiments depicted in FIGS. 3, 4, 5, 6, 7 and 8 can be integral to the body of the anatomic support for hand and wrist 1 or alternatively they can be rigidly fixed to it.

Any of the previous embodiments of the anatomic support for hand and wrist 1 of the present invention may be provided in a variety of sizes, in order to fit a variety of sizes of hands.

The anatomical feature of the upper surface 2 of the anatomic support for hand and wrist 1 is very advantageous for a user who uses a keyboard or the like, for the following reasons:

a) as both the wrist and the anterior portion of the palm of the hand of the user are permanently and anatomically supported by the anatomic support for hand and wrist 1, the tendons and muscles of the hands become more relaxed during typing operations, thereby reducing the risk from RSI-like injuries from occurring;

b) the use of the anatomic support for hand and wrist 1 makes all the muscles of the cervical and scapular chains work in a more relaxed way, as the weight of the hands is anatomically supported upon the anatomic support for hand and wrist 1, and therefore the shoulders of a person who operates a keyboard become more relaxed, thereby contributing to reduce the risk from RSI-like injuries from occurring;

c) by permanently and anatomically supporting both the wrist and the anterior portion of the palm of the hand of the user at a level substantially equal to the level of the keys of a keyboard, the anatomic support for hand and wrist 1 prevents the user from bending his/her hands upwardly or downwardly when is typing the keyboard, contributing to reduce the risk from RSI-like injuries from occurring;

d) by allowing the user to operate a mouse while keeping his/her hand permanently and anatomically supported, the anatomic support for hand and wrist 1 of the present invention prevents the user from bending his/her hands upwardly or downwardly when using a mouse, contributing to reduce the risk from RSI-like injuries from occurring;

e) the use of bottom protrusions provides low friction forces between the anatomic support for hand and wrist 1 and the surface where it rests, thereby facilitating the use of the anatomic support for hand and wrist 1 both to type on a keyboard or to operate a mouse.

Although the anatomic support for hand and wrist 1 has been described herein for use with a keyboard or a mouse of a computer, it should be mentioned that its use is not restricted to the above-mentioned pieces of equipment, as the support for hand and wrist 1 object of the present invention can be used in any situation where it is needed a support for both the hands and wrist of a user.

Therefore the anatomic support for hand and wrist 1 is not limited to the content of the above description, and it is only limited to the content of the appending claims.

The invention claimed is:

1. An anatomic support for hand and wrist comprising a body having an upper surface, a side surface and an inferior surface, the upper surface being provided with a shape that enables a user that operates a keyboard to place the hand on said upper surface so as to have the wrist and hand permanently and anatomically supported, said upper surface comprising: a front border protruding region, located at the front border portion of the upper surface and in contact with the central portion of the anterior part of the hand and serving to permanently provide an anatomic support for the anterior part of the palm of the hand of the user; a depressing segment of a generally concave shape, located at the center to back portion of the upper surface and encircling said front border protruding region, serving to permanently and anatomically accommodate the protruding back portion of the hand of the user; a back border upward segment, located at the back border portion of the upper surface and serving to permanently and anatomically accommodate the wrist of the user; and a side upward segment, located at the center to side border portion of the upper surface and serving to permanently and anatomically accommodate the external side portion of the anterior region of the palm of the user; said front border protruding region further comprising: a central segment, located at the central border section of the front border protruding region; a right descending segment, which descends from the central segment to the right side of the front border protruding region; a left descending segment, which descends from the central segment to the left side of the front border protruding region; and a central descending segment, which descends from the central segment to the center of the upper surface; the height of the side surface enables the user to keep the tip of his/her fingers at a level substantially equal to the level of the keys of the keyboard; said front protruding region, central depressing region, back border upward segment and the side upward segment cooperating to provide the upper surface with a shape that permanently and anatomically accommodate the anterior region of the palm of the hand and the wrist of the user; and the shape of said upper surface is able to conform the wrist and the anterior part of the palm of a hand among left and right hands of the user.

2. The anatomic support of claim 1 wherein an indicative signal is provided to inform to which hand it is intended to be used.

3. The anatomic support of claim 1 wherein said inferior surface is smooth.

4. The anatomic support of claim 3 wherein an indicative signal is provided to inform to which hand it is intended to be used.

5. The anatomic support of claim 1 wherein said inferior surface is provided with bottom protrusions.

6. The anatomic support of claim 5 wherein an indicative signal is provided to inform to which hand it is intended to be used.

7. The anatomic support of claim 6 wherein said bottom protrusions are integral to the inferior surface.

8. The anatomic support of claim 6 wherein said bottom protrusions are separate and rigidly connected to the inferior surface.

9. The anatomic support of claim 1 wherein the inner part of the body is hollow and the inferior surface is a rim portion.

10. The anatomic support of claim 9 wherein an indicative signal is provided to inform to which hand it is intended to be used.

11. The anatomic support of claim 10 wherein the inferior surface is provided with bottom protrusions.

12. The anatomic support of claim 10 wherein a hollow inner part of the body is provided with reinforcement ribs.

13. The anatomic support of claim 12 wherein the inferior surface is provided with bottom protrusions.

14. The anatomic support of claim 12 wherein bottom protrusions project from the reinforcement ribs.

15. The anatomic support of claim 14 wherein said bottom protrusions are integral to the body.

16. The anatomic support of claim 14 wherein said bottom protrusions are separate and rigidly connected to the body.

17. A pair of anatomic supports for hand and wrist each of the supports comprising a body having an upper surface, a side surface and an inferior surface, the upper surface being provided with a shape that enables a user that operates a keyboard to place the hand on said upper surface so as to have the wrist and hand permanently and anatomically supported, said upper surface comprising: a front border protruding region, located at the front border portion of the upper surface and in contact with the central portion of the anterior part of the hand and serving to permanently provide an anatomic support for the anterior part of the palm of the hand of the user; a depressing segment of a generally concave shape, located at the center to back portion of the upper surface and encircling said front border protruding region, serving to permanently and anatomically accommodate the protruding back portion of the hand of the user; a back border upward segment, located at the back border portion of the upper surface and serving to permanently and anatomically accommodate the wrist of the user; and a side upward segment, located at the center to side border portion of the upper surface and serving to permanently and anatomically accommodate the external side portion of the anterior region of the palm of the user; said front border protruding region further comprising: a central segment, located at the central border section of the front border protruding region; a right descending segment, which descends from the central segment to the right side of the front border protruding region; a left descending segment, which descends from the central segment to the left side of the front border protruding region; and a central descending segment, which descends from the central segment to the center of the upper surface; the height of the side surface enables the user to keep the tip of his/her fingers at a level substantially equal to the level of the keys of the keyboard; said front protruding region, central depressing region, back border upward segment and the side upward segment cooperating to provide the upper surface with a shape that permanently and anatomically accommodate the anterior region of the palm of the hand and the wrist of the user; and the shape of said upper surface of one of the supports of said pair being able to conform with the wrist and the anterior part of the palm of a left hand and the shape of said upper surface of the other of the supports of said pair being able to conform with the wrist and the anterior part of the palm of a right hand of the user.

18. The pair of anatomic supports of claim 17 wherein said inferior surface is smooth.

19. The pair of anatomic supports of claim 18 wherein said inferior surface is provided with bottom protrusions.

20. The pair of anatomic supports of claim 17 wherein the inner part of the body is hollow and the inferior surface is a rim portion.

21. The pair of anatomic supports of claim 20 wherein the inferior surface is provided with bottom protrusions.

22. The pair of anatomic supports of claim 20 wherein a hollow inner part of the body is provided with reinforcement ribs.

23. The pair of anatomic supports of claim 22 wherein bottom protrusions project from the reinforcement ribs.

24. The pair of anatomic supports of claim 17 wherein an indicative signal is provided in each of the pair to inform to which hand they are intended to be used.

* * * * *